United States Patent
Park

(10) Patent No.: US 11,986,338 B2
(45) Date of Patent: May 21, 2024

(54) MOBILE RADIOGRAPHY APPARATUS HAVING MULTIPLE POWER SUPPLIES

(71) Applicant: CARESTREAM HEALTH, INC., Rochester, NY (US)

(72) Inventor: Jangho Park, Fairport, NY (US)

(73) Assignee: Carestream Health, Inc., Rochester, NY (US)

(*) Notice: Subject to any disclaimer, the term of this patent is extended or adjusted under 35 U.S.C. 154(b) by 249 days.

(21) Appl. No.: 17/631,615

(22) PCT Filed: Aug. 25, 2020

(86) PCT No.: PCT/US2020/047711
§ 371 (c)(1),
(2) Date: Jan. 31, 2022

(87) PCT Pub. No.: WO2021/041358
PCT Pub. Date: Mar. 4, 2021

(65) Prior Publication Data
US 2022/0280131 A1 Sep. 8, 2022

Related U.S. Application Data

(60) Provisional application No. 62/891,992, filed on Aug. 27, 2019.

(51) Int. Cl.
*A61B 6/00* (2024.01)

(52) U.S. Cl.
CPC ............. *A61B 6/56* (2013.01); *A61B 6/4405* (2013.01)

(58) Field of Classification Search
CPC ....... A61B 6/4405; A61B 6/4411; A61B 6/56; A61B 6/03; A61B 6/4452; A61B 6/4458; A61B 6/4447
See application file for complete search history.

(56) References Cited

U.S. PATENT DOCUMENTS

2011/0123001 A1  5/2011  Kopcienski et al.

FOREIGN PATENT DOCUMENTS

| CN | 106456093 A | * | 2/2017 | ............. A61B 6/032 |
| JP | 2010-273827 | | 12/2010 | |

OTHER PUBLICATIONS

International Search Report mailed on Oct. 10, 2020 for International Application No. PCT/US2020/047711, 2 pages.

* cited by examiner

*Primary Examiner* — Don K Wong

(57) ABSTRACT

A mobile radiography apparatus includes a hybrid power supply system which includes batteries of different types. Each of the different type batteries is configured to supply electric power to a different portion of the mobile radiography apparatus. The different electric power supply characteristics of each the different battery types is matched to a corresponding power demand characteristic of one of the different portions of the mobile radiography apparatus.

14 Claims, 7 Drawing Sheets

MOBILE RADIOGRAPHY APPARATUS HAVING MULTIPLE POWER SUPPLIES

CROSS REFERENCE TO RELATED APPLICATIONS

This application claims the benefit of and is a U.S. National Phase filing of PCT Application PCT/US2020/047711 filed Aug. 25, 2020 entitled "MOBILE RADIOGRAPHY APPARATUS HAVING MULTIPLE POWER SUPPLIES", in the name of Jangho Park, which claims benefit of U.S. Patent Application Ser. No. 62/891,992, filed Aug. 27, 2019, in the name of Jangho Park., and entitled MOBILE RADIOGRAPHY UNIT HAVING MULTIPLE POWER SUPPLIES.

FIELD OF THE INVENTION

The invention relates generally to the field of medical imaging, and in particular to a portable radiographic imaging apparatus. More specifically, the invention relates to a mobile radiography apparatus having multiple power supplies.

BACKGROUND OF THE INVENTION

Mobile carts are employed in medical facilities to move medical equipment between locations. One type of mobile cart includes an x-ray source used to capture x-ray images on a digital x-ray detector. Medical x-ray images can be captured using various digital or analog techniques.

Mobile x-ray apparatus are of particular value in intensive care apparatus (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in mobile x-ray apparatus design to allow such devices to be more easily transported and/or operated. For a mobile/portable x-ray system, one challenge is to find an optimal battery solution that satisfies the power, runtime and service life needs of both the high-voltage components such as the x-ray source, or tube head, and/or x-ray generator and low-voltage subsystems such as a motor drive and computing electronics as against size, weight, power and cost factors involved.

The discussion above is merely provided for general background information and is not intended to be used as an aid in determining the scope of the claimed subject matter.

BRIEF DESCRIPTION OF THE INVENTION

A mobile radiography apparatus includes a hybrid power supply system having batteries of different types. Each of the different type batteries is configured to supply electric power only to a selected different portion of the mobile radiography apparatus. The different electric power supply characteristics of each the different battery types is matched to a corresponding power demand characteristic of one of the different portions of the mobile radiography apparatus.

In accordance with one embodiment, the present invention may provide a mobile radiography apparatus having a moveable transport frame and an x-ray source. At least two different power sources provide power for the apparatus. A first power source provides power for a first portion of the mobile x-ray radiography apparatus and a second power source provides power for a second portion of the mobile x-ray radiography apparatus. A drive mechanism may be configured to drive wheels to transport the apparatus.

In another embodiment, an x-ray radiography apparatus with an x-ray source includes at least two different power sources. A first power source is configured to provide power only to a first portion of the x-ray radiography apparatus and a second power source, different from the first power source, is configured to provide power only to a second portion of the x-ray radiography apparatus that does not include the first portion of the x-ray radiography apparatus.

In another embodiment, an x-ray radiography apparatus includes an x-ray source and electronic controls for the x-ray radiography apparatus. At least two different batteries provide power for the x-ray radiography apparatus. A first battery is configured to provide power only to a first portion of the x-ray radiography apparatus, and a second battery is configured to provide power only to a second portion of the x-ray radiography apparatus that does not include the first portion of the x-ray radiography apparatus.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. patent application Ser. No. 62/891,992, filed Aug. 27, 2019, in the name of Park, and entitled MOBILE RADIOGRAPHY UNIT HAVING MULTIPLE POWER SUPPLIES, which is hereby incorporated by reference herein in its entirety.

Figure 1:
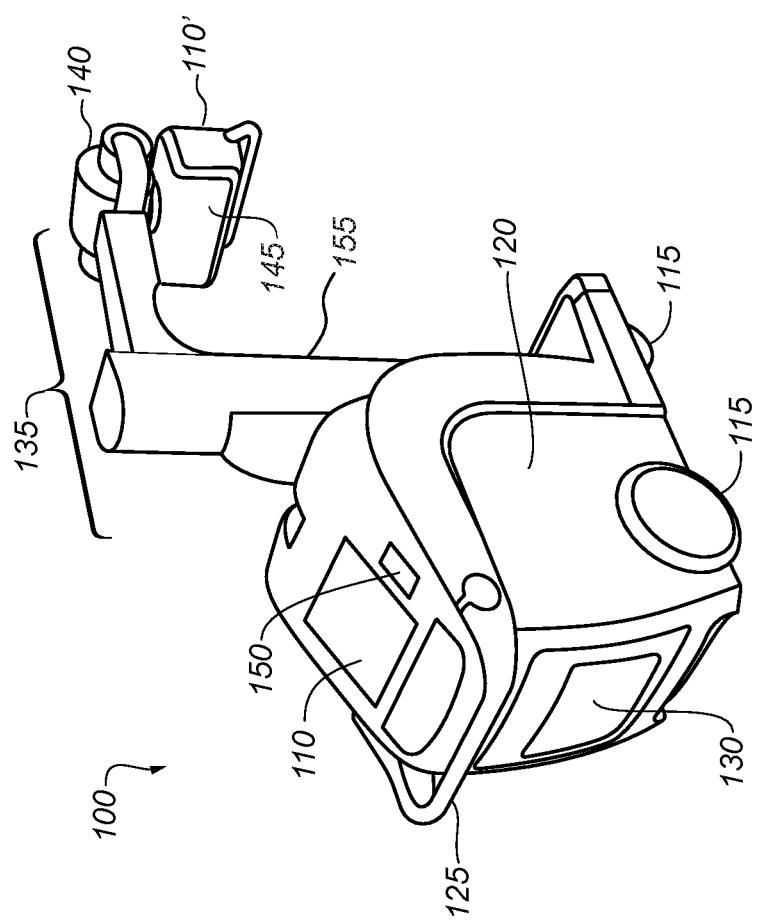
FIG. 1 is a diagram that shows a perspective view of a mobile radiography apparatus.

FIG. 1 shows a perspective view of a mobile radiography apparatus 100 having an x-ray source 140 for radiographically exposing patients. As shown in the figure, the mobile radiography apparatus 100 can include a moveable transport frame 120 that includes a first display 110 and an optional second display 110' attached to a collimator 145 to display relevant information such as captured images, an electronically controlled GUI and related data. As shown in the figure, the second display 110' and collimator can be pivotably mounted to the x-ray source 140 to be viewable/touchable from a 360 degree area. The displays 110, 110' can implement or control, via electronic touch screens, functions such as setting motor drive speeds, controlling the capturing, storing, transmitting, modifying, and printing of obtained radiographic images and can include an integral or separate control panel to assist in implementing such functions. For mobility, the mobile radiographic apparatus 100 can have one or more wheels 115 and one or more handle grips 125, typically provided at waist-level, arm-level, or hand-level, that help to guide the mobile radiographic apparatus 100 to its intended location.

A self-contained re-chargeable battery pack (FIG. 6) in the transport frame 120 or elsewhere can provide x-ray source exposure power, which can reduce or eliminate the need for operation near a power outlet. Further, the self-contained battery pack can provide power to a drive motor driving the wheels 115 for motorized transport of the mobile radiography apparatus 100. For storage, the mobile radiographic apparatus 100 can include an area/holder 130 for holding/storing one or more digital radiographic (DR) detectors or computed radiography (stimulated phosphor) cassettes for capturing radiographic images. The storage area 130 can be configured to hold a plurality of detectors and can also be configured to hold one size or multiple sizes of DR detectors or cassettes. Mounted to frame 120 is a support column 155 that supports an extendible arm 135 which, in turn, has attached thereto an x-ray source 140, also called an x-ray tube, tube head, or generator that can be mounted to the support arm 135. In another embodiment, the tube head or x-ray source 140 can be rotatably coupled to the support arm 135. In another exemplary embodiment, an articulated member of the support column 155 may bend at a joint mechanism. In another exemplary embodiment, support arm 135 may be configured to move vertically along support column 155 to allow movement of the x-ray source 140 over a range of vertical positions. Height settings for the x-ray source 140 can range from low height for imaging feet and lower extremities to shoulder height and above for imaging the upper body portions of patients in various positions. The mobile radiographic apparatus 100 can also include an electronic prep and expose control 150 for the x-ray source 140.

Figure 2:
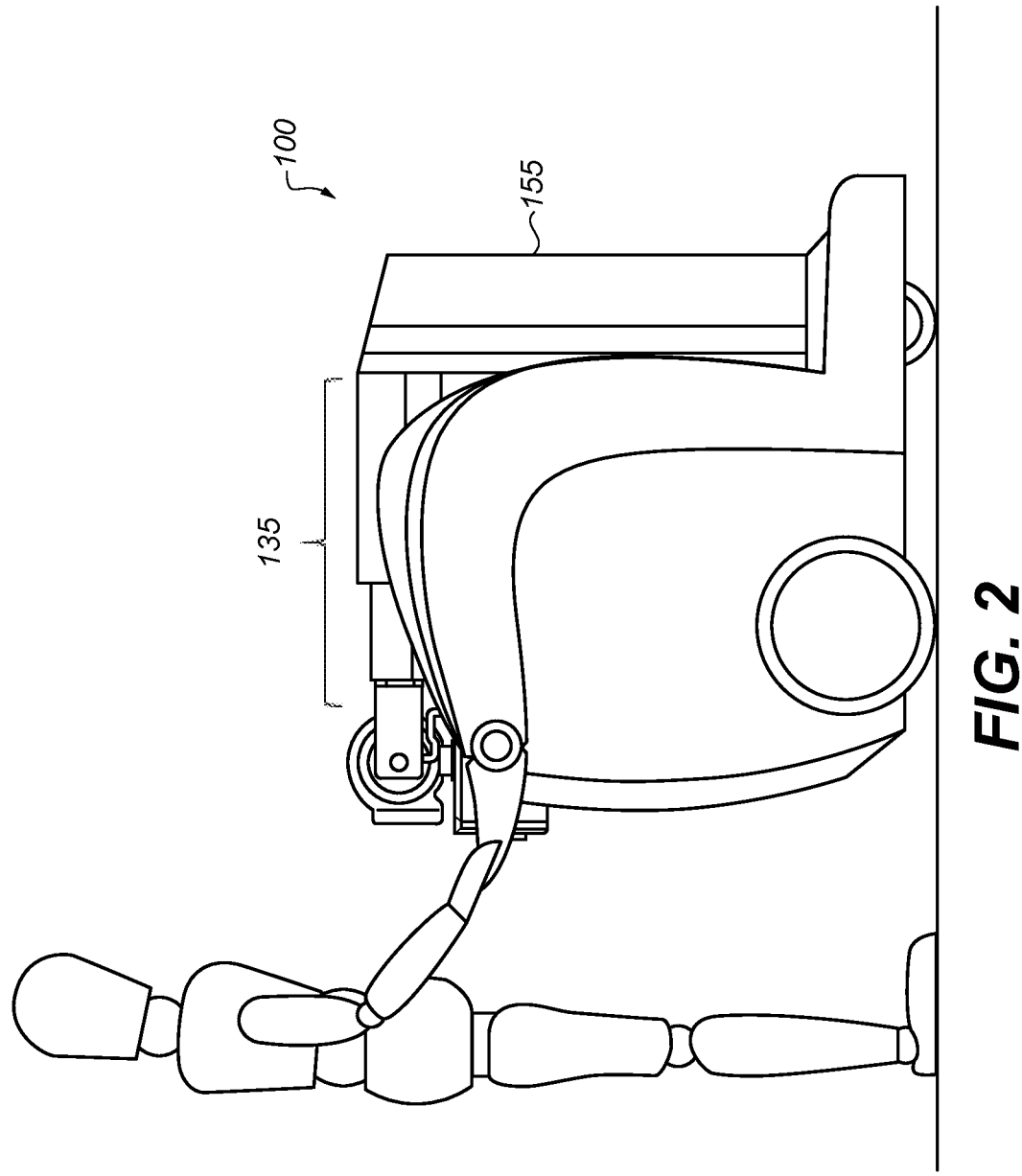
FIG. 2 is a diagram that shows another view of the mobile radiography apparatus of FIG. 1 in a docked position for travel.

As shown in FIG. 2, for ease during transport of the mobile radiographic apparatus 100, the support column 155 and support arm 135 can be moved and/or rotated to a docked position for easier motorized transport. When the mobile radiographic apparatus 100 is to be used for a patient exposure, the support column 155 and support arm 135 can be extended from the frame 120 for proper positioning by an operator, a user, or an x-ray technician.

Figure 3:
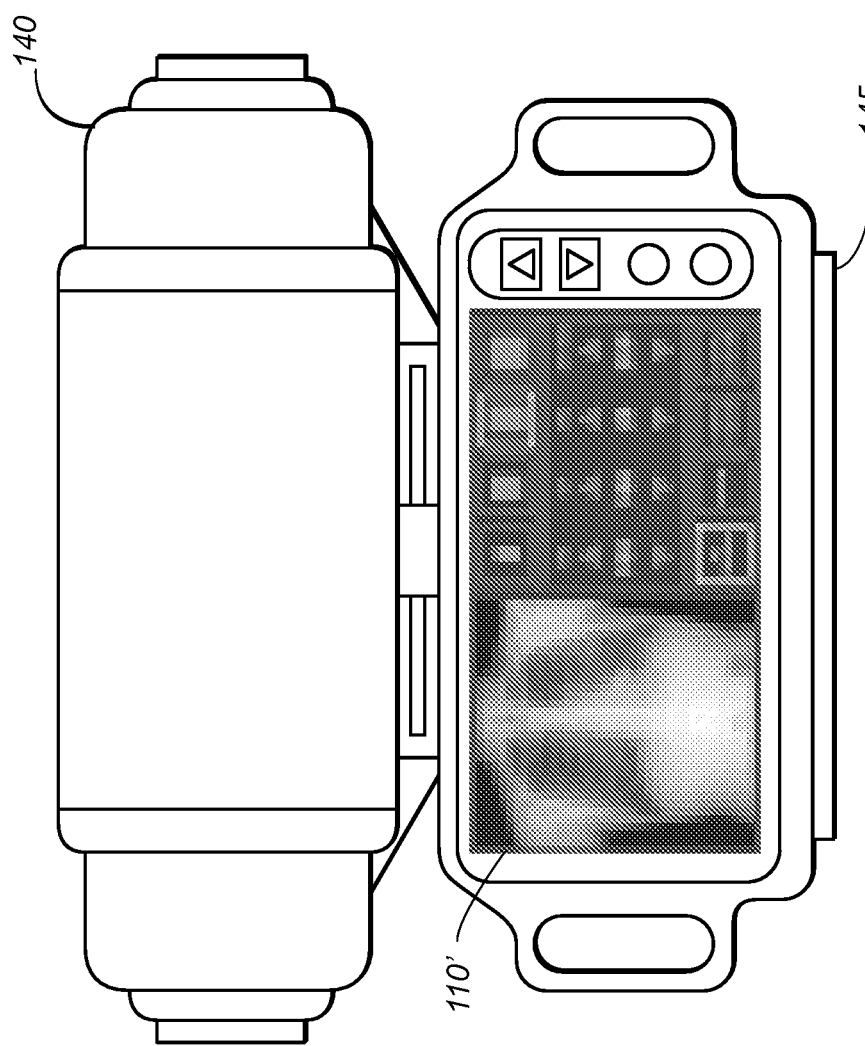
FIG. 3 is a diagram that shows an exemplary embodiment of an x-ray source, electronic controls screen, and collimator mounted to a boom assembly of a mobile radiography apparatus.

FIG. 3 is a diagram that shows an exemplary embodiment of the mobile radiographic apparatus control electronics implemented in a second display 110' mounted to a collimator 145 of an x-ray source 140 of the mobile radiography apparatus 100. In one embodiment, the collimator 145 is rotatably mounted to the x-ray source 140 so that the collimator can swivel. The second display 110' may also be mounted to the x-ray source 140 above the collimator 145.

According to exemplary embodiments of the application, the electronic displays 110, 110' can provide information such as but not limited to: (i) general information such as date, time, environment conditions, and the like; (ii) apparatus information such as model serial number, operating instructions, warning information, and the like; (iii) patient data, such as patient name, room number, age, blood type, and the like; (iv) indicators such as but not limited to power/battery indicators, detector status (e.g., on/off), wireless signal strength/connectivity, grid alignment aides, diagnostics and/or (v) imaging/procedure information, such as the exam type, exposure information, and the like.

According to embodiments of the application, the displays 110, 110', can provide electronic touch screen capabilities/functionality to the mobile x-ray imaging apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display generator/source current values and controls to change those values, such as: kVp, mA, mAs, Time, ECF, focal spot, collimator, filter, AEC, grid; (vi) display motor drive values and controls to change those values.

Figure 4:
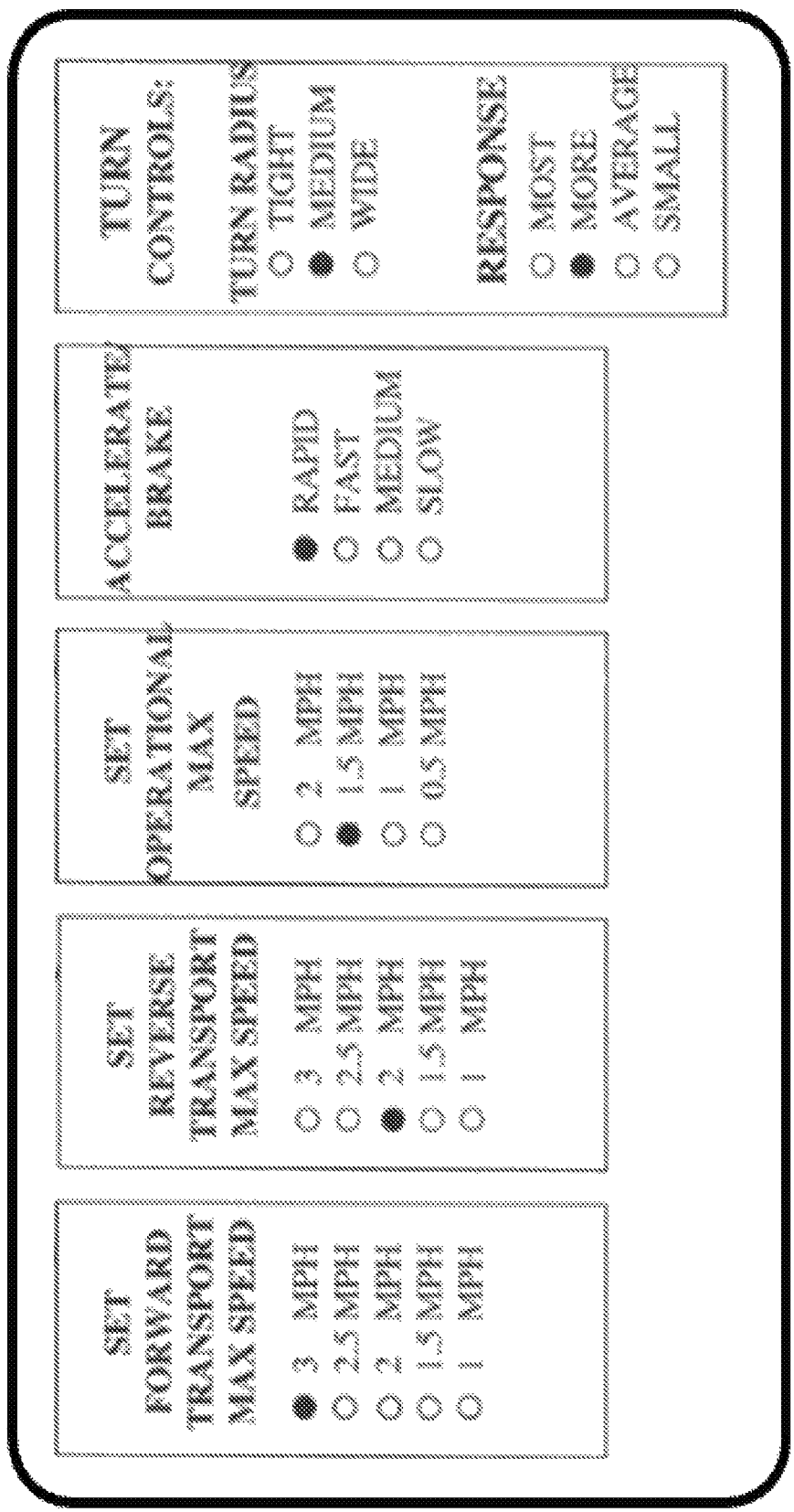
FIG. 4 is a diagram that illustrates an embodiment of a power setting screen for setting an operating profile of a motor drive control of the mobile radiography apparatus.

The mobile radiography apparatus 100 can include a first peak speed when the mobile radiography apparatus 100 is in transport (e.g., the support column 155 and arm 135 are in a docked position as shown in FIG. 2) and a second lower speed when the mobile radiography apparatus 100 is not in transport. As shown in FIG. 4, further control electronics of the mobile radiography apparatus 100 may be implemented in a user profile screen displayed on displays 110, 110' and can include a set forward transport maximum speed, a set reverse transport maximum speed, and a set operational maximum speed. Thus, each of the first top speed and the second top speed along with the reverse top speed can be modified by the user and stored in the mobile x-ray apparatus 100. The user profile screen can also include additional user profile settings for accelerate/brake transitions and turn controls. Further, when the tube head 140 is locked or docked in a travel configuration, the operator can selectively view a worklist on either of the displays 110, 110'. Power to provide the motor drive options disclosed in FIG. 4 may be provided by one or more batteries disposed in the transport frame 120 of the mobile radiography apparatus 100.

Figure 5:
FIG. 5 is a diagram that illustrates an embodiment of a current and voltage setting screen for controlling an energy level of the x-ray source.

FIG. 5 is a diagram that illustrates further control electronics of the mobile radiography apparatus 100 that may be implemented in an exemplary representative function on a touch screen display 110, 110', of the mobile x-ray imaging apparatus 100. As shown in FIG. 5, an example of electronic operator selectable x-ray source current controls and voltage controls is shown on a monitor of one or both of the displays 110, 110'. The operator may manually operate or use touch screen up/down arrows, as shown in FIG. 5, or manual knobs, to adjust current and voltage levels of the x-ray source 140.

Figure 6:
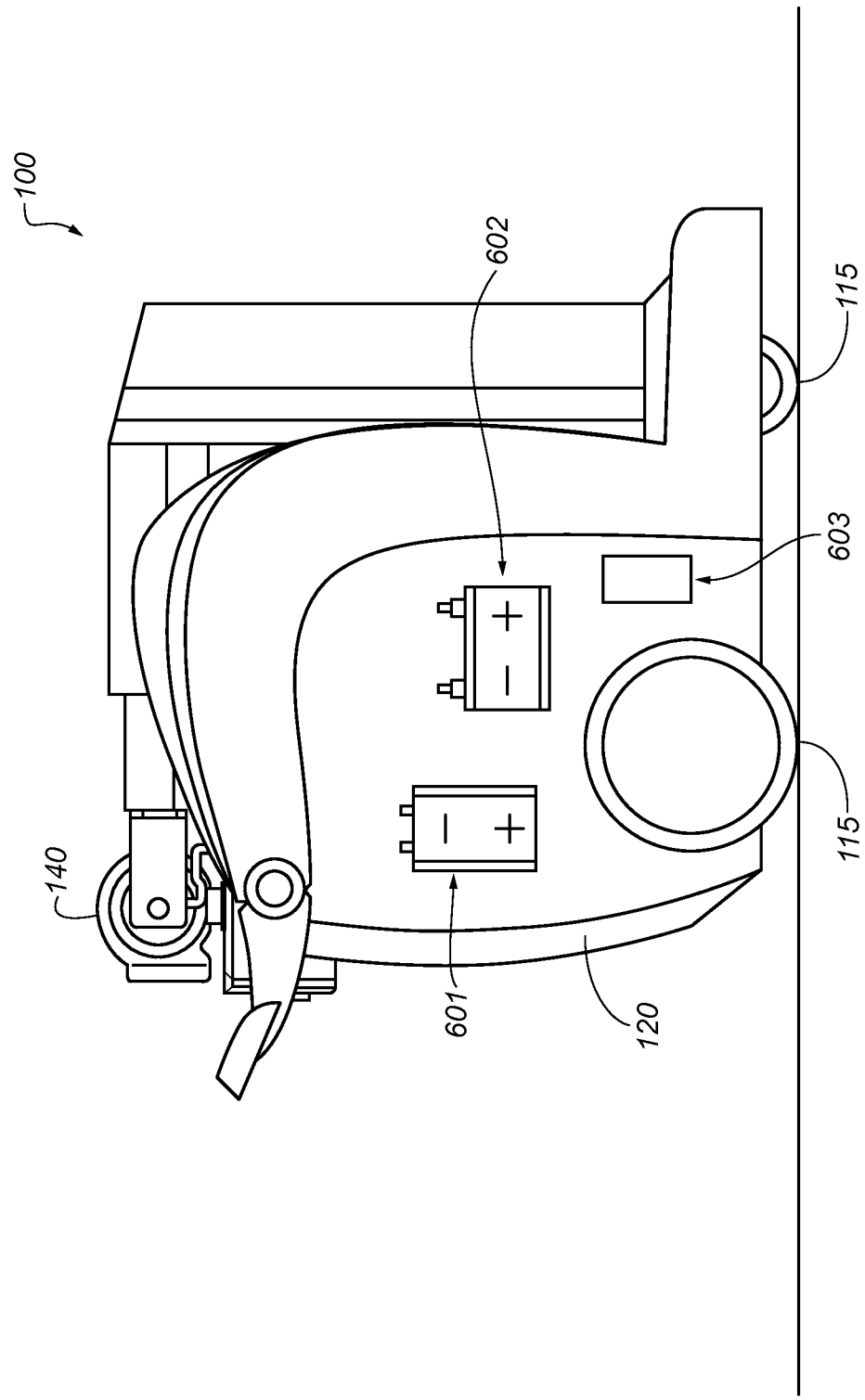
FIG. 6 is a schematic diagram of the mobile radiography apparatus of FIG. 1 showing at least two different types of batteries therein.

FIG. 6 illustrates the mobile radiography apparatus 100 having multiple power supplies of different types 601, 602, disposed within the transport frame 120 for supplying power each to different portion of the mobile radiography apparatus 100, such as battery 601 supplying power to the electronic drive system 603 for the wheels 115 and battery 602 supplying power to the x-ray source 140.

Having only one type of battery chemistry as the power supply of the mobile radiography apparatus 100, may result in satisfactory operation for certain attributes at the compromise of others. By selecting specific battery chemistries tailored to the needs of particular components, portions, or subsystems of the mobile radiography apparatus 100, a more optimal power supply solution can be achieved. Specifically, a lithium-based battery 601 and a lead-acid battery 602, for example, may be used in combination in the mobile radiography apparatus 100.

Lithium-based batteries 601 have high energy density, light weight, smaller safety envelope, low self discharge, high charge rate (for certain chemistries), moderate discharge rate, high cycle life, e.g., $LiFePO_4$ (LFP), and improved safety e.g., LFP and $Li_2TiO_3$ or $Li_4Ti_5O_{12}$ (LTO), but have a higher cost, require more safety protection electronics, are subject to transportation and safety regulation (for common lithium batteries). This battery type can be well suited for high cycle, low voltage subsystems like computing and control electronics. A majority of the total system battery capacity is used by the computing system, electronic display screens 110, 110', and associated electronics, including the motor drive control 603. This requires the need of a higher capacity battery system, at a lower weight, with low voltage (e.g., <48 VDC), high discharge cycles, fast charge times and continuous power draw.

Lead acid batteries 602 are low cost, have high discharge rates, are mature and well-understood technology that is widely available and durable. They have low energy density, are heavy, have limited discharge cycles, are sensitive to depth of discharge, are sensitive to temperature (>25° C.), and have a slow charge rate. These batteries can be well suited for x-ray source (high-voltage, high current) power requirements. The overall energy required for an x-ray exposure is relatively small and makes up only a fraction of the total mobile radiography system 100 power capacity needs. It does require high discharge rate but for short durations. By implementing a shallow depth of discharge with a larger size battery capacity, it can extend discharge cycles and service life. Since only a relatively small amount of capacity is required for x-rays, total charge time can be shorter vs. a whole system lead acid solution. Furthermore, the added weight of the lead-acid battery can also serve as ballast for the mobile radiography apparatus 100.

Figure 7:
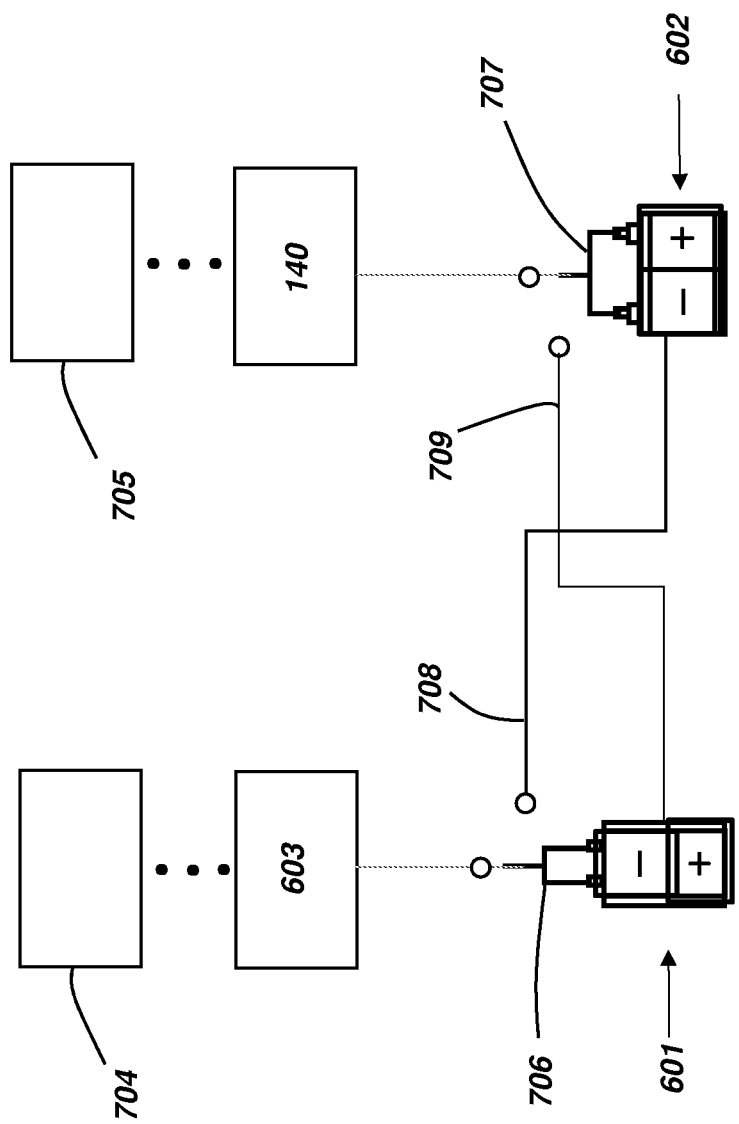
FIG. 7 is a schematic diagram of first and second type batteries connected to first and second portions, respectively, of the mobile radiography apparatus and connectable to each other for recharging.

FIG. 7 illustrates an exemplary lithium-based battery 601 electrically connected, using a switch or connector 706, to a motor drive system 603 for controlling drive wheels 115 of the mobile radiography apparatus 100. The lithium-based battery 601 may also be electrically connected to other selected portions or components 704 of the mobile radiography apparatus 100. Similarly, an exemplary lead-acid-based battery 602 is electrically connected, using a switch or connector 707, to an x-ray source or tube head 140 of the mobile radiography apparatus 100 for providing power thereto. The lead-acid-based battery 602 may also be electrically connected to other selected portions or components 705 of the mobile radiography apparatus 100.

The batteries 601, 602, may also be selectively connected to each other for recharging the batteries 601, 602. For example, switch or connector 706 from battery 601 may be selectively switched to conductive circuit 708 in order to supply current to recharge battery 602. Similarly, switch or connector 707 from battery 602 may be selectively switched to conductive circuit 709 in order to supply recharging current to battery 601. Alternatively, conductive circuits 708, 709, may be each selectively connected to connector 706, 707, respectively, to receive a recharging current without disconnecting connectors 706, 707, from their respective components or portions 603, 140, of the mobile radiography apparatus 100.

It should be noted that while the present description and embodiment examples may be partially directed to mobile radiographic medical imaging of a human or other subject, embodiments of the apparatus and methods of the present application can also be applied to other radiographic imaging applications. This includes applications such as non-destructive testing (NDT) and stationary radiographic imaging equipment, for which radiographic images may be obtained and provided.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A mobile x-ray radiography apparatus comprising:
a moveable transport frame;
an x-ray source; and
at least two different power sources, wherein a first one of the power sources is configured to provide power for a first portion of the mobile x-ray radiography apparatus and a second one of the power sources is configured to provide power for a second portion of the mobile x-ray radiography apparatus,
wherein the moveable transport frame comprises a motorized drive control, and wherein the first one of the power sources is configured to provide power for the motorized drive control, and
wherein the first one of the power sources is a non-lead-acid battery.

2. The apparatus of claim 1, wherein the second one of the power sources is configured to provide power for the x-ray source.

3. The apparatus of claim 2, wherein the second one of the power sources is a non-lithium battery.

4. The apparatus of claim 1, wherein the first one of the power sources is a lithium battery.

5. The apparatus of claim 2, wherein the second one of the power sources is a lead-acid battery.

6. The apparatus of claim 1, wherein the second one of the power sources is a non-lithium battery, and wherein the first one of the power sources and the second one of the power sources are configured such that the first power source recharges the second power source.

7. The apparatus of claim 1, wherein the second one of the power sources is a non-lithium battery, and wherein the first one of the power sources and the second one of the power sources are configured such that the second power source recharges the first power source.

8. An x-ray apparatus comprising:
   an x-ray source;
   electronic controls; and
   at least two different power sources, wherein a first one of the power sources is configured to provide power only to a first portion of the apparatus and a second one of the power sources is configured to provide power only to a second portion of the apparatus that does not include the first portion of the apparatus,
   wherein the first portion of the apparatus includes a motorized drive control for moving the apparatus, and
   wherein the first one of the power sources is a non-lead-acid battery.

9. The apparatus of claim 8, wherein the second portion of the apparatus includes the x-ray source.

10. The apparatus of claim 9, wherein the second one of the power sources is a non-lithium battery.

11. The apparatus of claim 8, wherein the first and second power sources are configured to be selectively electrically connectable so that one of the first or second power sources recharges the other one of the first and second power sources.

12. An x-ray apparatus comprising:
    electronic controls;
    an x-ray source; and
    at least two different batteries, wherein a first battery is configured to provide power only to a first portion of the x-ray apparatus, and wherein a second battery is configured to provide power only to a second portion of the x-ray apparatus that does not include the first portion of the x-ray apparatus,
    wherein the first portion of the x-ray apparatus includes electronically controlled motor driven wheels, and
    wherein the first battery is a non-lead-acid battery.

13. The apparatus of claim 12, wherein the second portion of the x-ray apparatus includes the x-ray source.

14. The apparatus of claim 12, wherein the first battery and the second battery are configured to be selectively electrically connectable so that one of the first battery or the second battery recharges the other one of the first battery and the second battery.

* * * * *